United States Patent
Akahori (10) Patent No.: US 7,024,029 B2
(45) Date of Patent: Apr. 4, 2006

(54) MEDICAL IMAGE PROCESSING METHOD AND APPARATUS

(75) Inventor: Sadato Akahori, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 681 days.

(21) Appl. No.: 09/987,361

(22) Filed: Nov. 14, 2001

(65) Prior Publication Data

US 2002/0122578 A1   Sep. 5, 2002

(30) Foreign Application Priority Data

Nov. 22, 2000 (JP) .............................. 2000-355338

(51) Int. Cl.
*G06K 9/00* (2006.01)

(52) U.S. Cl. ..................................................... 382/132

(58) Field of Classification Search ................ 382/128, 382/131, 132; 378/98–98.12, 37, 165; 600/407, 600/415

See application file for complete search history.

(56) References Cited

U.S. PATENT DOCUMENTS

| | | | | |
|---|---|---|---|---|
| 4,783,832 A * | 11/1988 | Kaneko | .................. | 382/164 |
| 6,374,131 B1 * | 4/2002 | Tomita et al. | .............. | 600/409 |
| 6,459,925 B1 * | 10/2002 | Nields et al. | ................ | 600/427 |
| 6,687,331 B1 * | 2/2004 | Muller et al. | .............. | 378/98.5 |
| 6,768,496 B1 * | 7/2004 | Bieger et al. | ................ | 345/630 |
| 2003/0208122 A1 * | 11/2003 | Melkent et al. | ............. | 600/426 |

* cited by examiner

*Primary Examiner*—Jingge Wu
*Assistant Examiner*—Ashutosh Upreti
(74) *Attorney, Agent, or Firm*—Sughrue Mion, PLLC (57) ABSTRACT

A medical image processing apparatus able to automatically superpose photographing information into image data obtained by radiography. The medical image processing apparatus includes a first unit for obtaining image data representing an image recorded by radiography; a second unit for obtaining photographing information data representing photographing information to be displayed on a screen; a third unit for determining position and size on the screen in which the photographing information represented by the photographing information data obtained by the second unit is to be displayed; and a fourth unit for adding the photographing information data to the image data or image attendant information which is attendant upon the image data, and outputting the added data.

18 Claims, 8 Drawing Sheets

MEDICAL IMAGE PROCESSING METHOD AND APPARATUS

BACKGROUND OF THE INVENTION

1. Field of the Invention

The present invention relates to a medical image processing method of superposing character data or image data into image data obtained by radiography, and a medical image processing apparatus using the medical image processing method.

2. Description of a Related Art

Photography using radiation (X-ray, α-ray, β-ray, γ-ray, electron beam, ultraviolet ray and so on) is conventionally utilized in various fields, and is one of most important means for a diagnosis particularly in a medical field. An X-ray radiography is variously improved since the realization of a first X-ray radiograph, and a method using combination of a fluorescent screen and an X-ray film is a main current at present. In recent years, various digitalized devices such as an X-ray CT, an ultrasonic diagnosis and an MRI are practically used in a medical image diagnosis, and construction of diagnostic information processing systems, etc. within hospitals is going to be advanced. Many researches for the digitalization have been also made with respect to an X-ray image, and radiography using a photostimulable phosphor is established and is practically used as a method to replace the conventional X-ray radiography.

Photostimulable phosphor (accumulating phosphor) is such substance that accumulates a part of radiation energy when irradiated with radiation and then generates photo-stimulated luminescence light in accordance with the accumulated energy when irradiated with excitation light such as a visible ray. Existence of the photostimulable phosphor was conventionally known. Radiography using the photostimulable phosphor is constructed as follows. That is, a radiation image of an object such as a human body is photographed and recorded on a sheet coated with the photostimulable phosphor. When the photostimulable phosphor sheet is scanned by excitation light such as a laser beam, photo-stimulated luminescence light is generated so that image data is obtained by photo-electrically reading the light. After the image data is suitably processed, an image represented by the image data is displayed on a display such as a CRT, or is printed on a film by a laser printer, etc. so that the radiation image can be displayed as a visible image.

Such radiography has performance equivalent to the conventional X-ray radiography in view of photographing sensitivity and image quality. For example, in comparison with the conventional X-ray radiography, an exposure area is very wide and a response of the photostimulated luminescence light to an exposure amount is approximately proportional to the exposure amount over the entire exposure area. Therefore, even when the object is photographed in any radiation amount, a luminescence area where the image exists can be grasped and normalized to be converted into a digital signal without under and over amounts. By combining the obtained signal with a suitable image processing method, an image of high quality can be steadily provided even under various kinds of photographing condition. Further, since the obtained image is stored as image data, a large amount of image data can be stored for a long time period without causing deterioration of the image, and developments to a medical diagnostic information system, etc. can be realized.

In the radiography, only one portion of the photographed object is photographed in many cases. For example, in the case of photographing breasts, the breasts are photographed plural times by changing a photographing direction with respect to each of left-hand and right-hand breasts. As a result, it is impossible to discriminate from which direction the X-ray images are obtained by photographing with respect to which breast when the X-ray images are merely seen at a diagnostic time. Therefore, in the conventional X-ray radiography, a character die formed by lead was taken together with the object into a photograph in order to display photographing condition such as an orientation of a patient or an incident direction of the X-ray at the photographing time within the X-ray image. Namely, the character die such as "R" representing the right and "L" representing the left is taken together with the object into the photograph so that a shadow of the character die is taken on the film. Accordingly, a diagnostician can easily discriminate a photographed portion, a photographing direction and so on. The character photographed in the X-ray image is called as a lead character.

In the radiography system for medicine using the photostimulable phosphor, character data or image data relative to photographing information and corresponding to the lead character as mentioned above is superposed into a digital image after image generation. However, according to the conventional method, work for superposing the data must be manually made every time. Therefore, when the data is often superposed, the efficiency is very low. Further, only the character data or the image data determined in advance can be superposed by such a way. Therefore, there was also a case where required character data was not prepared in some apparatuses.

SUMMARY OF THE INVENTION

The present invention was made in view of such problems. A first object of the invention is to provide medical image processing method and apparatus in which it is not necessary to manually superpose character or image data relative to photographing information into image data obtained by radiography, and the photographing information data is automatically added to the radiography image data and the added data is output. A second object of the invention is to provide medical image processing method and apparatus able to simply add arbitrary character data or image data.

To solve the above problems, a medical image processing method according to the present invention comprises the steps of: (a) obtaining image data representing an image recorded by radiography; (b) obtaining photographing information data representing photographing information to be displayed on a screen; (c) determining position and size on the screen in which the photographing information represented by the photographing information data obtained at step (b) is to be displayed; and (d) adding the photographing information data to one of the image data and image attendant information which is attendant upon the image data, and outputting the added data.

Further, a medical image processing apparatus according to the present invention comprises: first means for obtaining image data representing an image recorded by radiography; second means for obtaining photographing information data representing photographing information to be displayed on a screen; third means for determining position and size on the screen in which the photographing information represented by the photographing information data obtained by the second means is to be displayed; and fourth means for adding the photographing information data to one of the image data and image attendant information which is attendant upon the image data, and outputting the added data.

According to the invention, the photographing information required to make a medical diagnosis of the image can be automatically superposed into the image data obtained by the radiography. Further, according to the invention, arbitrary character or image data can be made and added to the image data obtained by the radiography. Accordingly, it is possible to efficiently make a medical image into which the required photographing information is superposed.

DESCRIPTION OF THE PREFERRED EMBODIMENTS

Embodiments of the present invention will now be described in detail with reference to the drawings. The same constituent elements are designated by the same reference numerals and explanation thereof will be omitted. In the following explanation, the information corresponding to conventional lead characters and superposed into an image so as to display photographing information is called as photographing information, and the data representing the photographing information is called as photographing information data. The photographing information data may include character data or image data.

Figure 1:
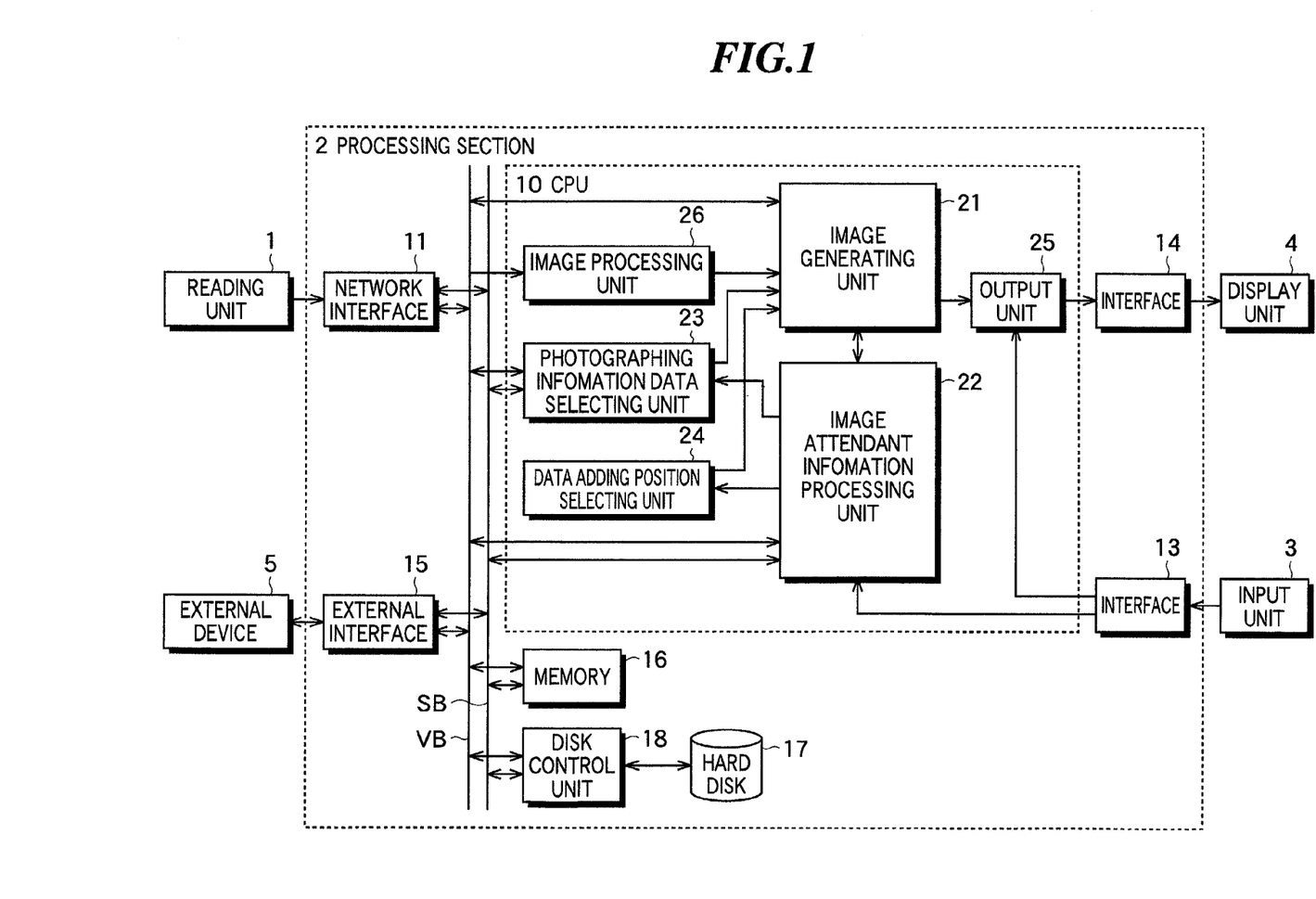
FIG. 1 is a view showing construction of a medical image processing system including a medical image processing apparatus according to a first embodiment of the invention.

FIG. 1 shows construction of a medical image processing system including a medical image processing apparatus according to a first embodiment of the invention.

In the embodiment, a recording sheet (photostimulable phosphor sheet) used in radiography is coated with a photostimulable phosphor substance, and records information of an object by being irradiated with radiation. The information recorded on the above recording sheet is photo-electrically read by a reading unit 1 and converted into image data. The image data and data attendant upon the image data (image attendant information) are transmitted to a processing section 2.

Here, the image attendant information is data attendant upon the image, and includes a name of a patient, a data size of the image, a scanning direction at a photographing time, photographing condition, etc. The photographing condition includes a photographed portion of the object at a time of radiography of the image, a photographing direction, i.e. an irradiating direction of the radiation, a method of photography, etc.

The processing section 2 receives the image data and the image attendant information, and performs various kinds of processing for displaying these image data and information as a visible image. Instructions executed by the processing section 2 and various kinds of information, etc. are input by an input unit 3 including a mouse or a keyboard. The visible image and the various kinds of information, etc. subjected to the image processing are displayed on a display such as a CRT or by a display unit 4 such as a printer. There is also a case if necessary where an externally attached recording medium or an external device 5 including an external computer connected to a network and a printer are connected to this system.

In the processing section 2, a central processing unit (hereinafter called as CPU) 10 is connected to each unit through a system bus SB or an image bus VB. The processing section 2 includes an internal memory 16, a hard disk 17 as a recording medium for recording a program and a database to be used for operation of the CPU 10, and a hard disk control unit 18. Further, the input unit 3 is connected to the CPU through an interface 13, and the display unit 4 is connected to the CPU through an interface 14. The reading unit 1 transmits and receives signals between the reading unit 1 and the CPU 10 through a network interface 11.

As the recording medium, a floppy disk, an externally attached hard disk, MO, MT, RAM, CD-ROM or DVD-ROM, etc. can be also used in addition to the built-in hard disk. It is also considered that the device externally arranged and connected to the network is used as an output destination of the visible image or the image data. The external device 5 including such a device transmits and receives signals between the CPU and the external device 5 through an external interface 15.

A functional block constructed by the CPU 10 and a program will next be explained.

An image generating unit 21 generates visible image data on the basis of image data received from the reading unit 1, data relative to selected photographing information and superposing position and size of the photographing information, and data of image attendant information, etc.

An image attendant information processing unit 22 executes processing for superposing the photographing information into the image in accordance with the image attendant information received from the reading unit 1 or a user's instruction. For example, when the image attendant information processing unit 22 extracts required data from the image attendant information, a photographing information data selecting unit 23 selects photographing information data corresponding to the required data from a stored database. Also, when the image attendant information processing unit 22 extracts the required data from the image attendant information, a data adding position selecting unit 24 selects the superposing position and size of the photographing information on the basis of the required data.

An output unit 25 outputs the data generated by the image generating unit 21 to the display unit 4, and the data is displayed as a visible image. In the case where the image processing is performed within the image processing apparatus, an image processing unit 26 performs image processing such as normalization, gradation processing and logic reading processing with respect to the input image data.

Figure 2:
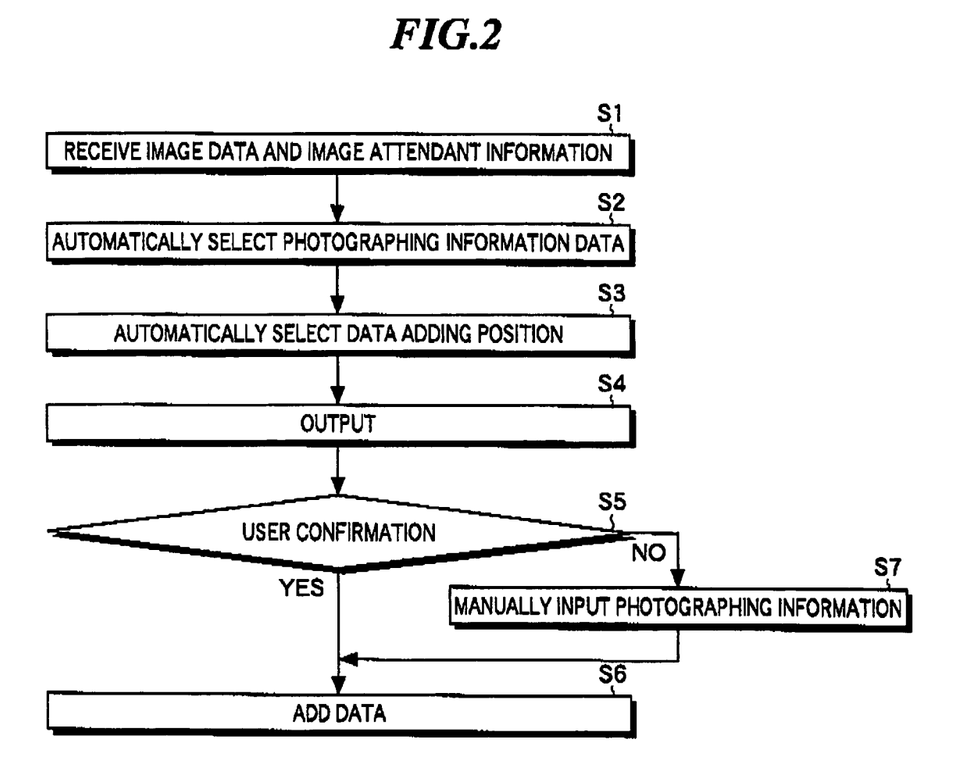
FIG. 2 is a flow chart showing a medical image processing method according to the first embodiment of the invention.

Next, an image processing method according to a first embodiment of the invention will be explained with reference to FIG. 2. FIG. 2 is a flow chart showing the image processing method according to this embodiment.

At step S1, image data and image attendant information are received. The image data and image attendant information may be used by receiving those generated in the external device or may be also generated within the image processing apparatus. Among those data, the image data is input to the image processing unit or the image generating unit, while the image attendant information is input to the image attendant information processing unit.

At step S2, the photographing information data selecting unit automatically selects photographing information data. For example, the photographing information data is selected on the basis of information relative to photographing condition for specifying the left-hand and right-hand sides of a photographed portion or the irradiating direction of an X-ray, etc. The information relative to the photographing condition may be constructed by one portion of the image attendant information received by the image attendant information processing unit or may be input from the input unit by a user. On the other hand, various kinds of photographing information data are stored for every photographing condition in advance in a database recorded on a hard disk. The photographing information data selecting unit first discriminates the received photographing condition, and reads corresponding photographing information data from the hard disk. The read photographing information data is processed in the image generating unit.

At step S3, the data adding position selecting unit automatically selects a data adding position of the photographing information and determines position data on the basis of another portion of the image attendant information input to the image attendant information processing unit. Namely, the data adding position selecting unit selects the adding position and size of the selected photographing information in a visible image and determines the position data on the basis of input data, e.g., an image scanning direction, a physical or logic size of the image, etc. The data is processed in the image generating unit.

At step S4, the image generating unit generates a picture formed by superposing the photographing information into the previously input image on the basis of the photographing information data selected by the photographing information data selecting unit and the position data determined in the data adding position selecting unit, and displays the picture in the display.

At step S5, the user sees and confirms the displayed image including the photographing information. At this time, if an image including desirable photographing information is obtained, the user can decide to superpose the photographing information. In this case, at step S6, the photographing information data displayed at that time and data relative to the position and the size of the photographing information are added to the image data of the image or the image attendant information.

To the contrary, when an image including desirable photographing information is not obtained at step S5, a user can manually add the photographing information, move the displayed photographing information and change the size of the photographing information at step S7. If an image including desirable photographing information is obtained by the manual operation, the photographing information data is added to the image data or the image attendant information at step S6.

Thereafter, the image including the photographing information may be printed on a film by a printer, or the image data and the image attendant information may be recorded to a hard disk or other recording media.

The photographing information data may be directly superposed into the image data, or may be added to the image data as the image attendant information so that the image and the photographing information are to be overlapped and displayed at an outputting time.

Further, a selection as to whether or not the photographing information is directly superposed into the image may be changed by a device at an output destination. In the case where the device at the output destination has a function of superposing the photographing information data into the image data on the basis of the image attendant information, the image data and the image attendant information are respectively stored. To the contrary, in the case where the device at the output destination has not the above-mentioned function, the photographing information data is superposed into the image data and the superposed image data is stored.

According to this embodiment, the photographing information can be automatically superposed into the image on the basis of the photographing condition of the image photographed by radiation. Accordingly, even when the number of images, into which the photographing information is superposed, is increased, the processing can be performed without greatly taking time and labor.

Next, a medical image processing apparatus according to a second embodiment of the invention will be explained.

Figure 3:
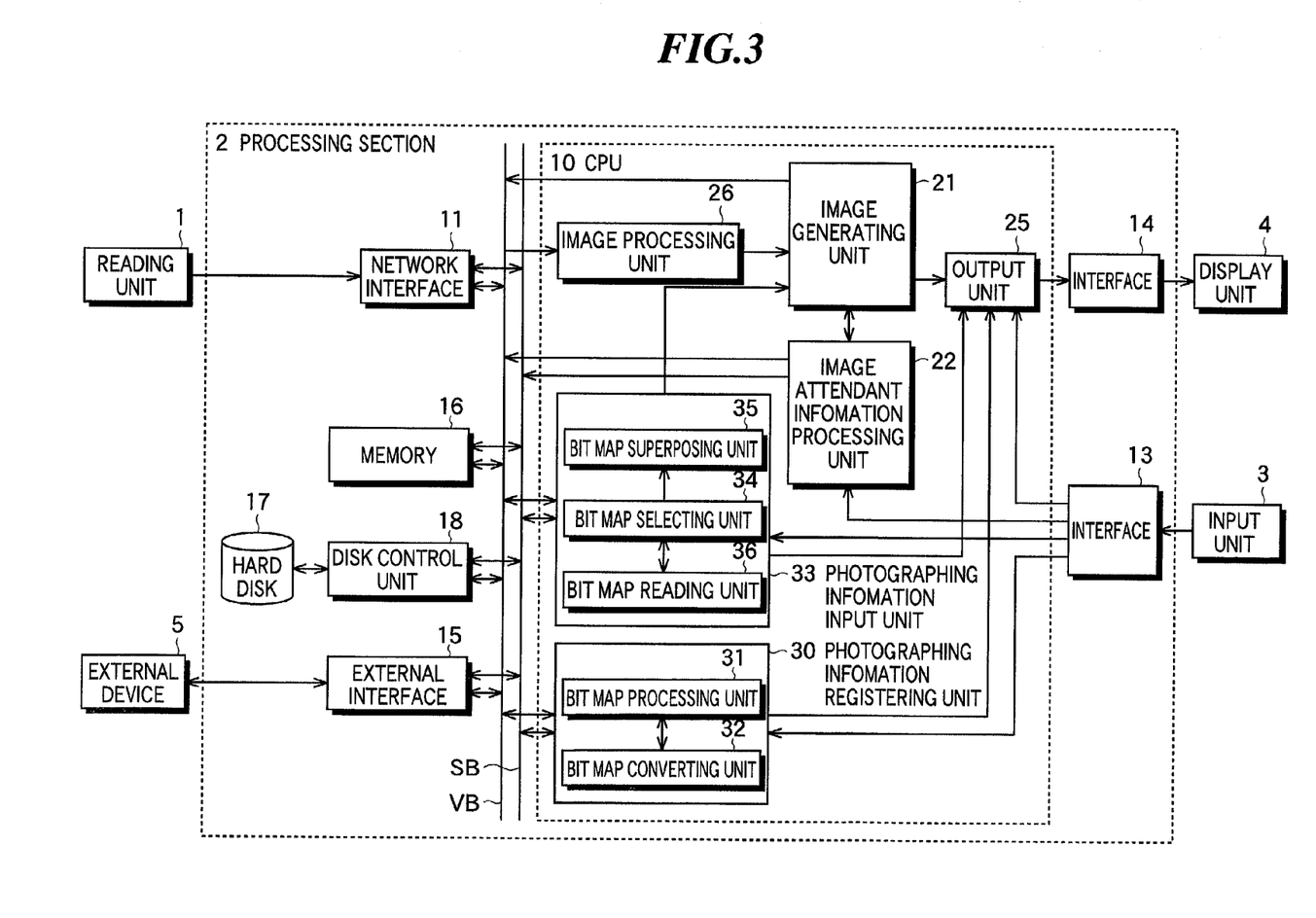
FIG. 3 is a view showing construction of a medical image processing system including a medical image processing apparatus according to a second embodiment of the invention.

FIG. 3 shows construction of a medical image processing system including the medical image processing apparatus according to the second embodiment of the invention. In FIG. 3, there are added a photographing information registering unit 30 for registering arbitrary photographing information made by a user, and a photographing information input unit 33 for use of inputting instruction for selecting photographing information to be superposed from the registered photographing information. The photographing information registering unit 30 includes a bit map converting unit 32 for converting a plurality of characters input by the user as to the photographing information into image data so as to obtain photographing information data, and a bit map processing unit 31 for processing the obtained photographing information data to output the processed photographing information data so that the obtained photographing information is displayed. The photographing information input unit 33 includes a bit map reading unit 36 for reading the registered photographing information data so that the registered photographing information is displayed, a bit map selecting unit 34 for selecting the photographing information data in accordance with the user's instruction, and a bit map superposing unit 35 for superposing the selected photographing information data into the image data.

Next, a medical image processing method according to the second embodiment of the invention will be explained.

Figure 4:
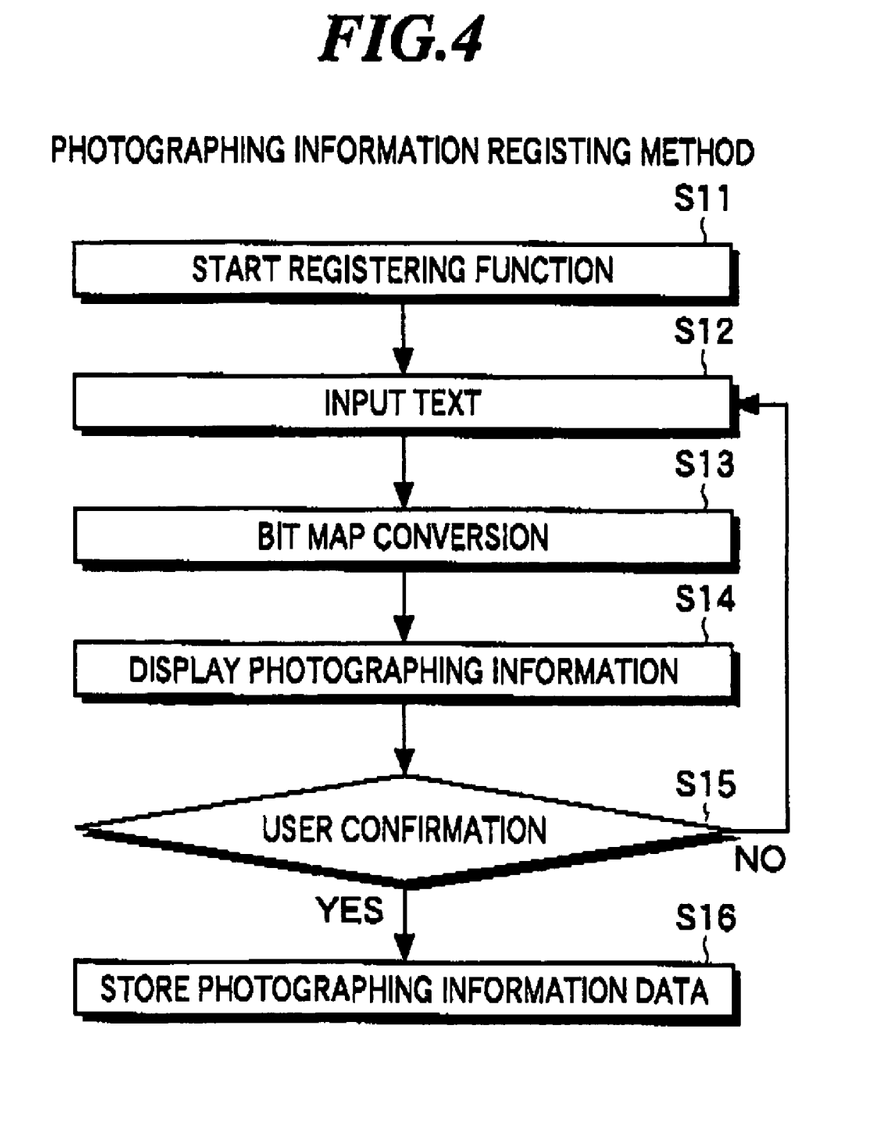
FIG. 4 is a flow chart showing a photographing information registering method within a medical image processing method according to the second embodiment of the invention.

In this embodiment, the user can register required photographing information in advance before the photographing information is superposed into an image. FIG. 4 is a flow chart showing a registering method of the photographing information in this embodiment.

At step S11, a function of registering the photographing information is started in accordance with instruction input to the input unit. At step S12, a plurality of characters for the photographing information to be used is input. At step S13, the input characters are converted into a bit map by the bit map converting unit 32 as shown in FIG. 3. At step S14, the photographing information converted into the bit map is displayed in the display through the bit map processing unit 31 as shown in FIG. 3. At step S15, the user confirms this photographing information. If there is no error in this photographing information, the photographing information data is stored on a recording medium at step S16. To the contrary, if there is any error in the photographing information and the user wants to re-input a plurality of characters at step S15, it is returned to step S12 and a plurality of characters can be re-input.

Figure 5:
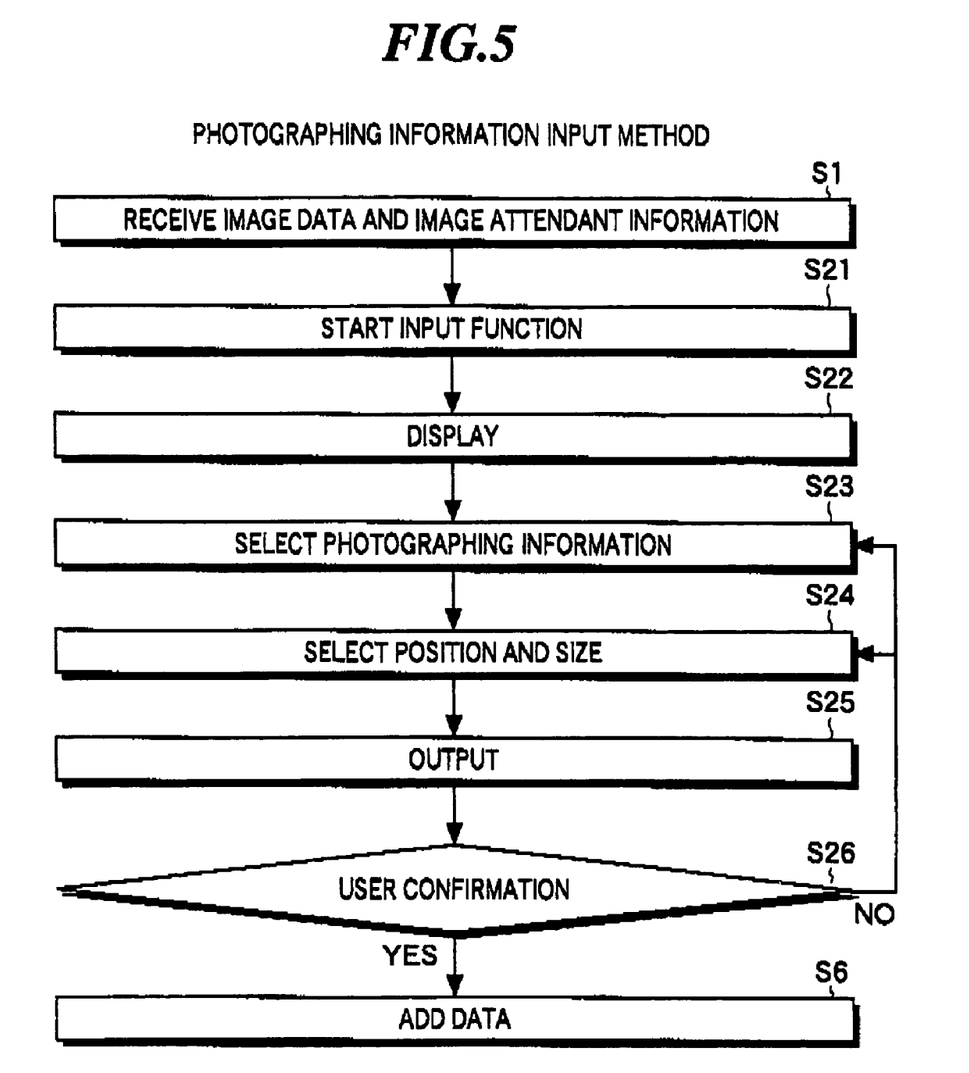
FIG. 5 is a flow chart showing a photographing information inputting method within the medical image processing method according to the second embodiment of the invention.

A method for superposing the photographing information into an image will next be explained. FIG. 5 is a flow chart showing a photographing information inputting method in this embodiment.

At step S1, image data and image attendant information are received. The image data and image attendant information maybe used by receiving those generated by the external device, or may be also generated within the image processing apparatus. At step S21, a photographing information inputting function is manually started in accordance with instruction input to the input unit. At step S22, the bit map reading unit 36 as shown in FIG. 3 reads a list of registered and stored photographing information converted into the bit map so that it is displayed in the display.

At step S23, while the user sees the screen, the user selects desirable photographing information from the displayed list of photographing information. At step S24, the user also selects desirable position and size of the photographing information in the image. The user can freely select the position and size of the photographing information by designating them in the display by using a mouse, etc. The photographing information data of the selected photographing information is transmitted to the image generating unit together with data relative to the superposing position and size of the photographing information. At step S25, the image generating unit superposes the photographing information into the image data and outputs the superposed data so that the superposed image is displayed in the display.

At step S26, the user sees the displayed image and confirms the photographing information. At this time, if an image including the desirable photographing information is obtained, the user decides to superpose the photographing information. At step S6, the photographing information data is added to the image data in the bit map superposing unit 35. To the contrary, if an image including the desirable photographing information is not obtained, it is again returned to step S23 or S24 and the photographing information or the position and size of the photographing information can be reselected. At step S6, the decided photographing information data may be added to the image attendant information.

Although the input characters are converted into a bit map in this embodiment, the input characters can be converted into image data in another format to be also used.

According to this embodiment, since arbitrary photographing information can be superposed into an arbitrary position of the image by registering the photographing information in advance by the user, a visible image can be made in accordance with a specification which conforms to each facility or user.

Next, a medical image processing method according to a third embodiment of the invention will be explained. In this embodiment, the medical image processing method according to the first embodiment of the invention and the medical image processing method according to the second embodiment of the invention are combined with each other. Namely, according to this embodiment, both a function of automatically superposing the photographing information in accordance with the photographing condition and a function of manually simply superposing arbitrary photographing information can be realized.

Figure 6:
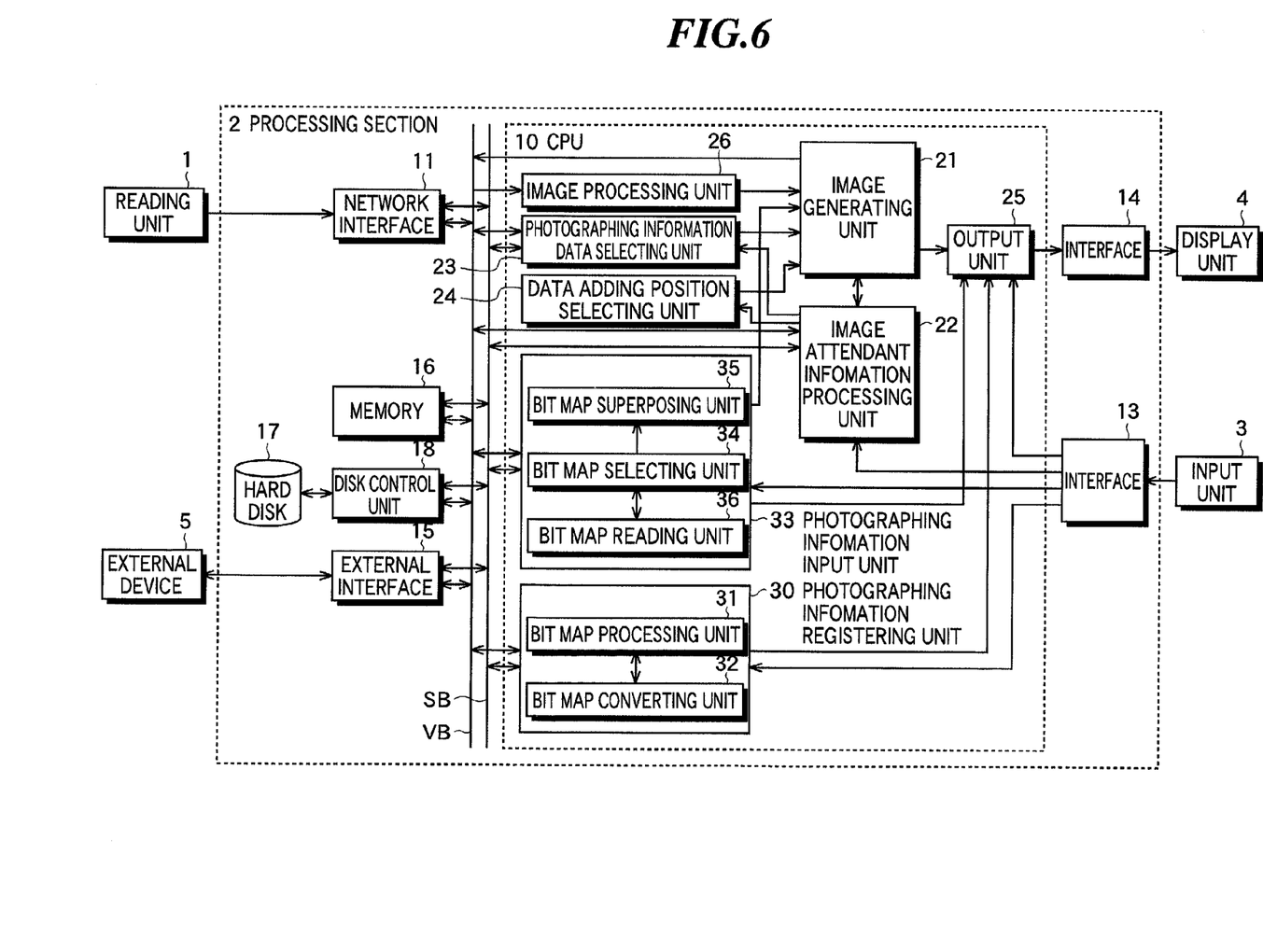
FIG. 6 is a view showing construction of a medical image processing system including a medical image processing apparatus according to a third embodiment of the invention.

FIG. 6 shows construction of a medical image processing system including a medical image processing apparatus according to the third embodiment of the invention. This image processing apparatus includes a photographing information data selecting unit 23 for automatically selecting the photographing information, a data adding position selecting unit 24 for automatically selecting adding position and size of the photographing information, a photographing information registering unit 30 for registering arbitrary photographing information, and a photographing information input unit 33 for use of inputting instruction for selecting photographing information to be superposed from the registered photographing information.

Figure 7:
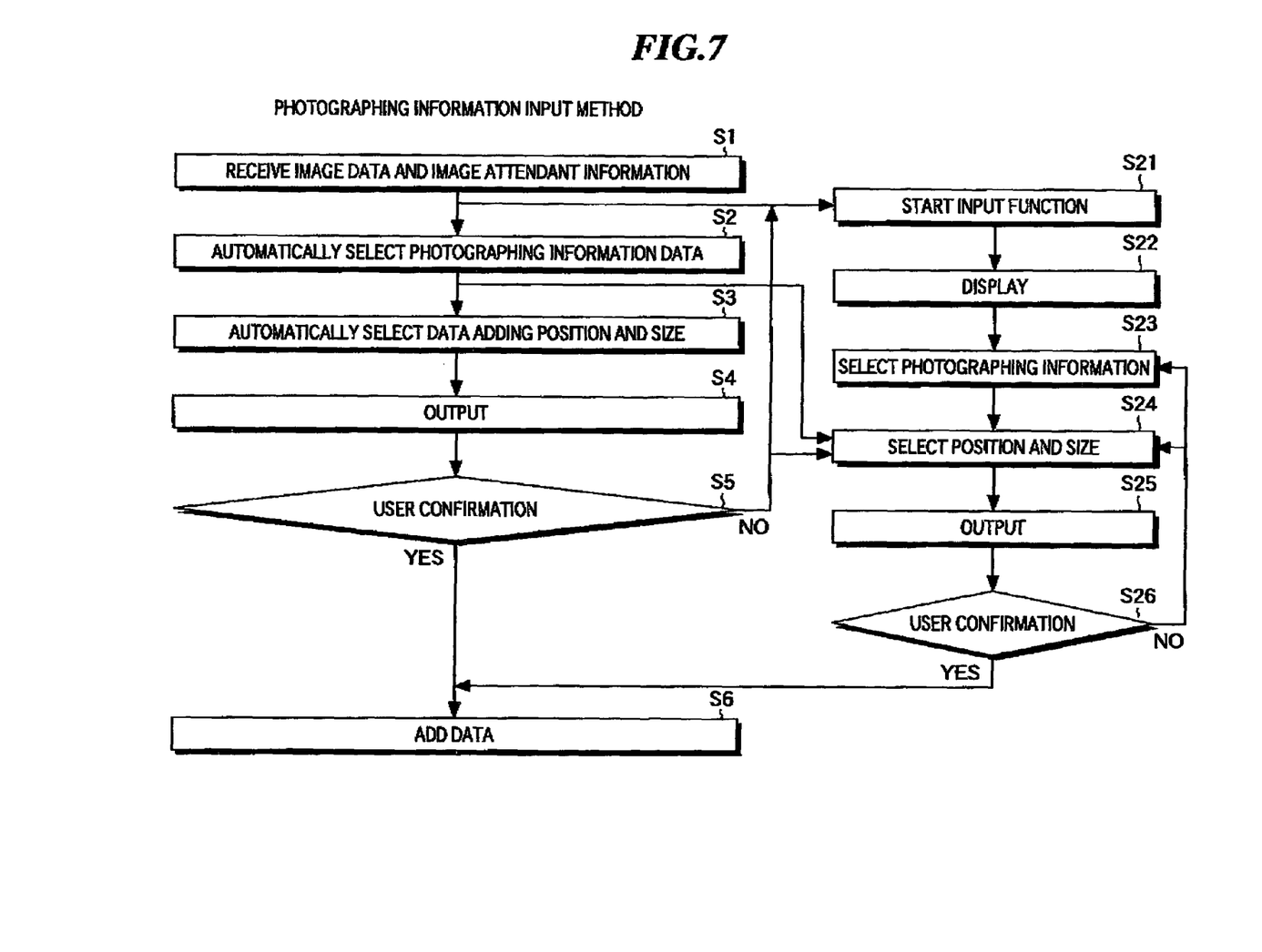
FIG. 7 is a flow chart showing a medical image processing method according to the third embodiment of the invention.

FIG. 7 is a flow chart showing a medical image processing method according to the third embodiment of the invention. As shown in FIG. 7, at step S1, image data and image attendant information are received. Thereafter, a user can select (1) superposing of the photographing information using an automatic selection at step S2 or (2) manual superposing of the photographing information at step S21. In the case where the photographing information is manually superposed, as a list of the photographing information displayed at step S22, the photographing information registered in advance by the user as in the image processing method according to the second embodiment may be displayed, or data stored in advance for the automatic selection may be displayed, or both the registered photographing information and the stored data may be displayed. Further, even after the photographing information is automatically selected, the adding position and size of the photographing information can be manually selected at step S24. Further, even after the position and size of the photographing information are determined by the automatic selection and the photographing information is superposed, the user can confirm the photographing information at step S5 so that it proceeds to step S21 or S24 at which the photographing information can be arbitrarily superposed.

According to this embodiment, for example, in the case where the same photographing information is superposed into plural images, time and labor can be greatly reduced by using the automatic selecting function in the superposing of the photographing information. Further, since the image processing apparatus has a function of making arbitrary photographing information and superposing the arbitrary photographing information by the user, the photographing information necessary for the user can be reliably provided.

The image processing apparatus according to the present invention can be also embodied as one portion of a system including a medical image reader and an image display unit. Such a system will next be explained with reference to FIG. 8.

Figure 8:
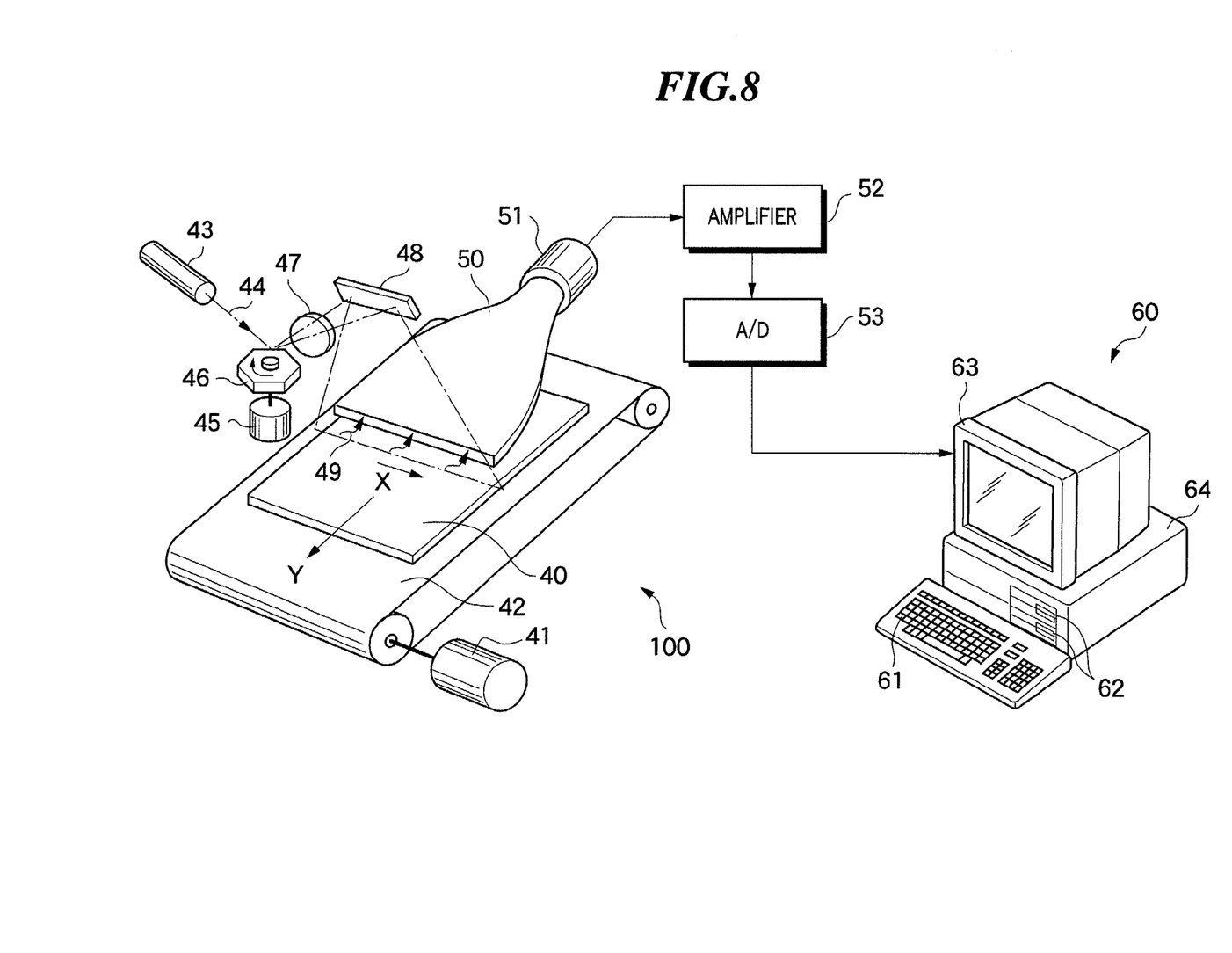
FIG. 8 is a view showing construction of the system in which the medical image processing apparatus according to the invention, a medical image reader and an image display unit are combined.

In the medical image reader 100 as shown in FIG. 8, a photostimulable phosphor sheet 40, on which a radiation image is recorded, is set to a predetermined position thereof. The photostimulable phosphor sheet 40 is conveyed in Y-direction by a sheet conveying means 42 driven by a motor 41. On the other hand, a light beam (excitation light) 44 emitted from a laser beam source 43 is reflected and deflected by a rotary polygon mirror 46 rotated by a motor 45 at high speed in an arrow direction, and passes through a convergent lens 47. Thereafter, an optical path of the light beam 44 is changed by a mirror 48 and the photostimulable phosphor sheet 40 is scanned by the light beam 44 in X-direction. The light beam 44 is irradiated to the photostimulable phosphor sheet 40 by this scanning, and photostimulated luminescence light 49 of an amount according to accumulated and recorded radiation image information is generated from an irradiated portion. The photostimulated luminescence light 49 is guided along an optical guide 50, and is photo-electrically detected by a photomultiplier (multiplier phototube) 51. An analog signal output from the photomultiplier 51 is amplified by an amplifier 52, and is digitized by an A/D converter 53. This digital signal is transmitted as image data to an image processing apparatus 60.

The image processing apparatus 60 includes an input unit 61 having a keyboard or a mouse for inputting instructions and information, a driving section 62 for operating a floppy disk, etc. as an auxiliary recording medium, and a main body 64 having a central processing unit (CPU), an internal memory, a hard disk as a recording medium, an interface for transmitting and receiving signals between the image reader and the CPU, and so on. An image display unit 63 such as a CRT for displaying a visible image on the basis of image data is connected to the image processing apparatus 60.

When the image data is received by the image processing apparatus 60, image data including the superposed photographing information and subjected to suitable image processing according to an object is generate by the CPU, and recorded on a hard disk, etc for storage. When the image is displayed, the image data is selectively read by the CPU. After the image processing is performed, the image data is output to the image display unit 63. Further, the image is output on a film, etc. by using a printer, etc. so that the output results are supplied for diagnosis.

According to the present invention, with respect to the image data obtained by the radiography, it is possible to automatically superpose into the image the photographing information required for a medical diagnosis using the image. Further, by adding a function of registering arbitrary photographing information and a function of manually superposing the photographing information, the required photographing information can be simply made and superposed into the image even in the case where the photographing information is different among users or facilities.

The invention claimed is:

1. A medical image processing method comprising the steps of:
   (a) obtaining image data representing an image recorded by radiography and image attendant information which is attendant upon the image data and includes information with respect to photographing condition of the image recorded by radiography;
   (b) automatically selecting photographing information data representing photographing information to be superposed into the image from a database on the basis of the information with respect to photographing condition of the image recorded by radiography;
   (c) selectively determining position and size on the image in which the photographing information represented by the photographing information data selected at step (b) is to be superposed; and
   (d) adding the photographing information data to one of the image data and the image attendant information and outputting the added data.

2. A medical image processing method according to claim 1, wherein:
   step (a) includes generating the image data by reading the image recorded by radiography and generating the image attendant information including information with respect to photographing condition of the image recorded by radiography.

3. A medical image processing method according to claim 1, wherein:
   step (b) includes automatically selecting one kind of photographing information data from plural kinds of photographing information data stored in said database on the basis of the information with respect to photographing condition.

4. A medical image processing method according to claim 1, wherein:
   step (a) includes receiving the image data representing the image recorded by the radiography and read by an image reader, and the image attendant information including information with respect to photographing condition of the image recorded by radiography.

5. A medical image processing method according to claim 4, wherein the image attendant information further includes information with respect to a size of the image and information with respect to rotation and/or inversion of the image.

6. A medical image processing method comprising the steps of:
   (a) converting a plurality of characters input in accordance with plural kinds of photographing condition into plural kinds of image data;
   (b) storing the plural kinds of image data as plural kinds of photographing information data;
   (c) obtaining image data representing an image recorded by radiography;
   (d) selecting photographing information data representing photographing information to be superposed into the image from said plural kinds of photographing information data;
   (e) selectively determining position and size on the image in which the photographing information represented by the photographing information data selected at step (d) is to be superposed; and
   (f) adding the photographing information data to one of the image data and image attendant information which is attendant upon the image data, and outputting the added data.

7. A medical image processing method according to claim 1, wherein step (d) includes superposing the photographing information into the image in accordance with the position and the size on the image determined at step (c), and outputting image data representing the superposed image.

8. A medical image processing method according to claim 1, wherein step (d) includes adding the photographing information data to the image attendant information and outputting the added data.

9. A medical image processing method according to claim 1, further comprising the step of changing the photographing information data selected at step (b).

10. A medical image processing apparatus comprising:
    first means for obtaining image data representing an image recorded by radiography and image attendant information which is attendant upon the image data and includes information with respect to photographing condition of the image recorded by radiography;
    second means for automatically selecting photographing information data representing photographing information to be superposed into the image from a database on the basis of the information with respect to photographing condition of the image recorded by radiography;

third means for selectively determining position and size on the image in which the photographing information represented by the photographing information data selected by said second means is to be superposed; and fourth means for adding the photographing information data to one of the image data and the image attendant information and outputting the added data.

11. A medical image processing apparatus according to claim 10, wherein:

said first means generates the image data by reading the image recorded by the radiography and generates the image attendant information including information with respect to photographing condition of the image recorded by radiography.

12. A medical image processing apparatus according to claim 10, wherein:

said second means automatically selects one kind of photographing information data from plural kinds of photographing information data stored in said database on the basis of the information with respect to photographing condition.

13. A medical image processing apparatus according to claim 10, wherein:

said first means receives the image data representing the image recorded by the radiography and read by an image reader, and the image attendant information including information with respect to photographing condition of the image recorded by radiography.

14. A medical image processing apparatus according to claim 13, wherein the image attendant information further includes information with respect to a size of the image and information with respect to rotation and/or inversion of the image.

15. A medical image processing apparatus comprising:

first means for converting a plurality of characters input in accordance with plural kinds of photographing condition into plural kinds of image data;

second means for storing the plural kinds of image data as plural kinds of photographing information data;

third means for obtaining image data representing an image recorded by radiography;

fourth means for selecting photographing information data representing photographing information to be superposed into the image from said plural kinds of photographing information data;

fifth means for selectively determining position and size on the image in which the photographing information represented by the photographing information data selected by said fourth means is to be superposed; and sixth means for adding the photographing information data to one of the image data and image attendant information which is attendant upon the image data, and outputting the added data.

16. A medical image processing apparatus according to claim 10, wherein said fourth means superposes the photographing information into the image in accordance with the position and the size on the image determined by said third means, and outputs image data representing the superposed image.

17. A medical image processing apparatus according to claim 10, wherein said fourth means adds the photographing information data to the image attendant information and outputs the added data.

18. A medical image processing apparatus according to claim 10, further comprising means for changing the photographing information data selected by said second means.

* * * * *